United States Patent
Jeong (10) Patent No.: US 11,224,769 B2
(45) Date of Patent: Jan. 18, 2022

(54) THERAPEUTIC ULTRASONIC WAVE GENERATING DEVICE

(71) Applicant: CLASSYS INC., Seoul (KR)

(72) Inventor: Seong Jai Jeong, Seoul (KR)

(73) Assignee: CLASSYS INC., Seoul (KR)

( * ) Notice: Subject to any disclaimer, the term of this patent is extended or adjusted under 35 U.S.C. 154(b) by 904 days.

(21) Appl. No.: 15/780,083

(22) PCT Filed: Oct. 4, 2016

(86) PCT No.: PCT/KR2016/011039
§ 371 (c)(1),
(2) Date: May 30, 2018

(87) PCT Pub. No.: WO2017/095008
PCT Pub. Date: Jun. 8, 2017

(65) Prior Publication Data
US 2018/0353778 A1    Dec. 13, 2018

(30) Foreign Application Priority Data

Dec. 1, 2015 (KR) .................. 10-2015-0169848
Aug. 12, 2016 (KR) .................. 10-2016-0102979

(51) Int. Cl.
*A61N 7/02* (2006.01)
*A61N 7/00* (2006.01)
*A61B 8/00* (2006.01)

(52) U.S. Cl.
CPC .................. *A61N 7/02* (2013.01); *A61N 7/00* (2013.01); *A61B 8/4461* (2013.01);
(Continued)

(58) Field of Classification Search
None
See application file for complete search history.

(56) References Cited

U.S. PATENT DOCUMENTS

2002/0062080 A1    5/2002  Okawa et al.
2002/0062081 A1    5/2002  Okawa et al.
(Continued)

FOREIGN PATENT DOCUMENTS

KR    2002-0038558 A    5/2002
KR    10-0823213 B1    4/2008
(Continued)

OTHER PUBLICATIONS

International Search Report dated Jan. 6, 2017, issued in counterpart International Application No. PCT/KR2016/011039 (2 pages, including annex).

*Primary Examiner* — Katherine L Fernandez
*Assistant Examiner* — Michael S Kellogg
(74) *Attorney, Agent, or Firm* — Westerman, Hattori, Daniels & Adrian, LLP (57) ABSTRACT

The present invention relates to a therapeutic ultrasonic wave generating device. The present invention includes: a rotating motor; an ultrasonic wave generating unit being provided with a transducer generating ultrasonic waves; and a focus rotation movement unit moving the focus of the ultrasonic waves generated by the ultrasonic wave generating unit in a circle on the same plane by receiving a transmission of rotational force of the rotating motor. The present invention enables: the focus of ultrasonic waves to be moved in the circle having a constant radius at a uniform depth under the skin; and energy to be applied uniformly and evenly within the movement radius, thereby enabling enhancement of therapeutic performance.

15 Claims, 4 Drawing Sheets

(52) U.S. Cl.
CPC ............... *A61N 2007/0008* (2013.01); *A61N 2007/0056* (2013.01); *A61N 2007/0065* (2013.01); *A61N 2007/0086* (2013.01); *A61N 2007/0091* (2013.01)

(56) References Cited

U.S. PATENT DOCUMENTS

| | | | | |
|---|---|---|---|---|
| 2005/0119577 A1* | 6/2005 | Taniguchi | ............ | A61B 8/4461 600/459 |
| 2009/0171252 A1* | 7/2009 | Bockenstedt | ........ | G10K 11/352 601/2 |

FOREIGN PATENT DOCUMENTS

| | | | | |
|---|---|---|---|---|
| KR | 10-2010-0120188 A | 11/2010 | | |
| KR | 10-2011-0091831 A | 8/2011 | | |
| KR | 10-1177691 B1 | 8/2012 | | |
| KR | 101177691 B1 * | 8/2012 | ............... | A61N 7/02 |
| KR | 10-1365946 B1 | 2/2014 | | |
| KR | 10-2015-0060644 A | 6/2015 | | |

\* cited by examiner

THERAPEUTIC ULTRASONIC WAVE GENERATING DEVICE

TECHNICAL FIELD

The present invention relates to a therapeutic ultrasonic wave generating device and, more particularly, to a therapeutic ultrasonic wave generating device enabling the focus of ultrasonic waves to be moved in a circle at a uniform depth under the skin and thus uniformly distributing the ultrasonic waves within the skin, thereby allowing therapeutic performance for obesity to be enhanced.

BACKGROUND ART

Recently, as dietary life has became westernized, with a rapid rise in obesity, obesity has become one of the major causes damaging health and beauty nationally. Accordingly, various diet programs and ultrasonic wave devices for treatment of obesity have been developed and are widely used An obesity treatment technique of a High Intensity Focused Ultrasound (HIFU) was originally used for the purpose of anticancer therapy by destroying cancer cells by selectively and noninvasively targeting tumors of internal organs which were coagulated at high temperature. Later, Solta Medical of the USA developed a device called Liposonix with a built-in HIFU which was the first apparatus specifically designed to reduce human abdominal obesity. A process of fat-shattering by using a HIFU is to cause a tissue temperature to be risen to 65° C.~100° C. at a moment when a focused ultrasound is focusing on a designated point of a fat cell, thereby destroying the tissue. An HIFU device causes coagulation necrosis of fat to occur noninvasively by focusing HIFU energy on a selected part without causing any harm on a skin surface, which is different from, for example, laser and high frequency RF equipment used in the dermatology field. The fat necrosed as such is naturally removed by a restoration mechanism of our body.

As a known ultrasound obesity treatment device, there is Korean Patent No. 10-1365946 (Publication date: Feb. 24, 2014), 'High Intensity Focused Ultrasound Generating Device for the Deduction of Fat Tissue.'

The 'High Intensity Focused Ultrasound Generating Device for the Deduction of Fat Tissue' forces ultrasound waves to permeate inside skin by driving a transducer on a pivot after moving the transducer to a desired position in X axis and Y axis directions.

However, the 'High Intensity Focused Ultrasound Generating Device for the Deduction of Fat Tissue' has a problem that ultrasound waves are supplied to a curved surface (circular arc) due to the characteristics of the pivot point driving when the ultrasound is supplied by the pivot point driving, whereby uniform treatment is not accomplished because energy supplied to skin is reduced and a depth of a focal point is changed as periphery of the curved surface is approached.

DISCLOSURE

Technical Problem

Accordingly, the present invention has been made keeping in mind the above problems occurring in the prior art, and an object of the present invention is to provide an ultrasonic wave generating device enabling the focus of ultrasonic waves to be moved in a circle at a uniform depth under the skin and thus uniformly distributing the ultrasonic waves within the skin, thereby allowing therapeutic performance for obesity treatment to be enhanced.

Technical Solution

In order to accomplish the above object, the present invention provides a therapeutic ultrasonic wave generating device. The device according to an embodiment of the present invention includes: a rotating motor; an ultrasonic wave generating unit provided with a transducer generating ultrasonic waves; and a focus rotation movement unit moving the focus of the ultrasonic waves generated by the ultrasonic wave generating unit in a circle on the same plane by receiving a transmission of rotational force of the rotating motor.

Advantageous Effects

As described above, the present invention has an advantage over the conventional art in that the focus of ultrasonic waves is enabled to be moved on the same plane at a uniform depth under the skin and thus energy can be applied uniformly within the part to be treated, thereby allowing therapeutic performance to be enhanced.

The present invention has an advantage over the conventional art in that the focus of ultrasonic waves is enabled to form a circle having a constant radius at a uniform depth under the skin and thus energy is applied uniformly within the movement radius, thereby allowing therapeutic performance to be further enhanced.

*Description of major reference numerals in the drawings*.

| | |
|---|---|
| 100: Rotating motor | 110: Motor shaft |
| 200: Ultrasonic wave generating unit | |
| 300: Focus rotation movement unit | |
| 310: Rotation plate part | |
| 310a: Bearing insertion part | |
| 310b: Axial hole | |
| 311: First rotation plate body | |
| 312: Second rotation plate body | |
| 320: Protruding part | |
| 330: Support part | 331: Bearing |
| 332: Support body | |
| 332a: Bearing stationary shaft | |
| 332b: Ball body | 332c: Ball support fixture |
| 333: First supporter | 334: Second supporter |
| 333a: First magnet | 333b: Second magnet |
| 400: Header housing unit | |
| 410: Motor insertion unit | |
| 420: Motor fastening bracket part | |
| 420a: Shaft through tube | |
| 500: Cartridge casing unit | |
| 500a: Ultrasonic wave penetration unit | |
| 500b: Ultrasonic wave generating space | |
| 510: Base plate installation part | |
| 520: External casing part | |

*Description of major reference numerals in the drawings*.

521: First ultrasonic wave penetration window
530: Internal casing part
531: Second ultrasonic wave penetration window
600: Division part
610: Division film body
700: First PCB
710: Second PCB

BEST MODE

The present invention will be described in detail with reference to the accompanying drawings. In describing the present invention, repeated descriptions, known functions which have been deemed to obfuscate the gist of the present invention, and detailed descriptions on the construction will be omitted below. The embodiments of the present invention are intended to fully describe the present invention to a person having ordinary knowledge in the art to which the present invention pertains. Accordingly, the shapes, dimensions, etc. of components in the drawings may be exaggerated to emphasize a clearer description.

Figure 1:
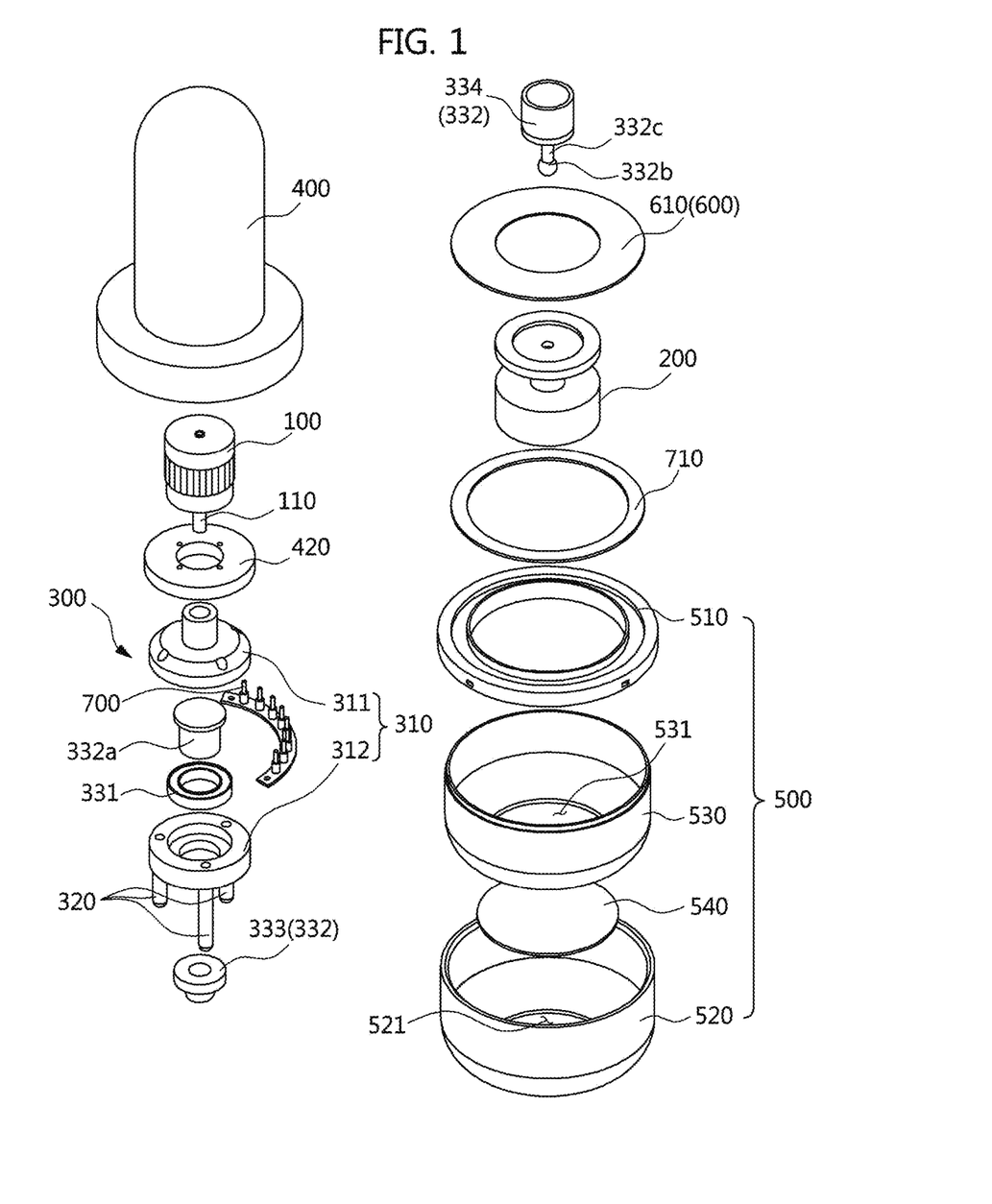
FIG. 1 is an exploded perspective view illustrating an embodiment of a therapeutic ultrasonic wave generating device according to the present invention.
Figure 2:
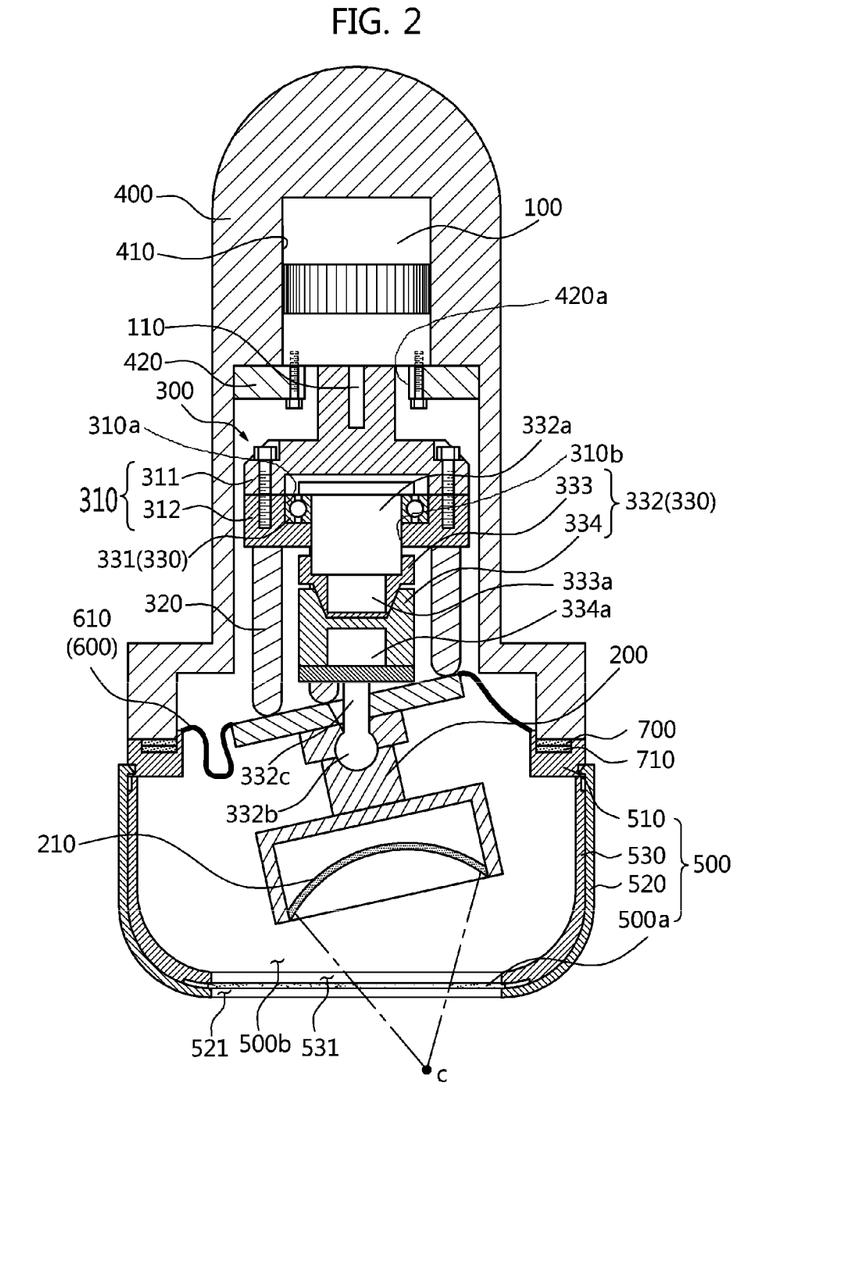
FIG. 2 is a cross-sectional view illustrating an embodiment of a therapeutic ultrasonic wave generating device according to the present invention.

FIG. 1 is an exploded perspective view illustrating an embodiment of a therapeutic ultrasonic wave generating device according to the present invention, and FIG. 2 is a cross-sectional view illustrating an embodiment of a therapeutic ultrasonic wave generating device according to the present invention.

With reference to FIGS. 1 and 2, the therapeutic ultrasonic wave generating device according to the present invention includes: a rotating motor 100 generating rotational force by being supplied with electrical power; and an ultrasonic wave generating unit 200 being provided with a transducer 210 generating ultrasonic waves by being supplied with electrical power In addition, the ultrasonic wave generating unit 200 includes a focus rotation movement unit 300 moving the focus C of the ultrasonic wave generated by the ultrasonic wave generating unit 200 in a circle on the same plane by receiving a transmission of rotational force of the rotating motor.

The therapeutic ultrasonic wave generating device according to the present invention may further include: a header housing unit 400 being installed with the rotating motor 100 therein; and a cartridge casing unit 500 being installed with the ultrasonic wave generating unit 200 therein.

The housing unit 400 in the present invention is illustrated as having a top thereof in a closed shape as illustrated in FIG. 1. However, the header housing unit 400 may be connected to a main body (not shown) by a cable (not shown).

The cable such as above may play a role to control an operation of the ultrasonic wave generating unit 200 through a signal transmitted from the main body by connecting the main body and the ultrasonic wave generating unit 200 to be described later to each other.

The cartridge casing unit 500 is provided with an ultrasonic wave penetration unit 500a of a transparent or translucent material through which the ultrasonic waves pass in a direction that the ultrasonic waves are emitted from the ultrasonic wave generating unit 200, wherein the ultrasonic wave penetration unit 500a may be a transparent film or translucent film, as an example.

The focus rotation movement unit 300 forces the ultrasonic wave generating unit 200 to be continuously tilted at a center of the motor shaft 110 of the rotating motor 100 at an equal degree angle with rotational force of the rotating motor 100 by being disposed between the rotating motor 100 and the ultrasonic wave generating unit 200, thereby moving the focus C of the ultrasonic wave generated by the ultrasonic wave generating unit 200 in a circle on the same plane, as an example.

An embodiment of the therapeutic ultrasonic wave generating device according to the present invention will be described in more detail as follows.

A motor insertion unit 410 in which the rotating motor 100 is inserted is provided inside the header housing unit 400, a shaft through hole 420a which the motor shaft 110 of the rotating motor 100 passes through is formed on an inlet of the motor insertion unit 410, and motor fastening bracket part 420 fastening the rotating motor 100 inserted in the motor insertion unit 410 is coupled with the header housing unit 400.

The motor fastening bracket part 420 pressurizes a body of the rotating motor 100 by coupling with and fastening to the header housing unit 400 with a commonly known coupling structure such as a bolt, a screw, and so on, thereby fastening the rotating motor 100 inside the motor insertion unit 410, as an example. Accordingly, the motor fastening bracket part 420 may fasten a position of the rotating motor 100 by being coupled with and fastened to the header housing unit 400 with a structure having, for example, a tight fit, or may also implement various modifications capable of fastening the rotating motor 100 with commonly known other examples, as is clearly stated here.

The focus rotation movement unit 300 includes: a rotation plate part 310 being rotated by being coupled with the motor shaft 110 of the rotating motor 100; a plurality of protruding parts 320 being disposed separately from each other on the rotation plate part 310, protruding with different heights from each other, and having each end thereof being in contact with the ultrasonic wave generating unit 200, thereby forcing the ultrasonic wave generating unit to be tilted based on an axial direction of the motor shaft 110; and a support part supporting the ultrasonic wave generating unit 200 to force the ultrasonic wave generating unit 200 to be continuously tilted at an equal degree angle by a rotation of the rotation plate part 310, as an example.

The plurality of protruding parts 320 is each disposed at an equal distance from a rotating center of the rotation plate part 310, as an example.

A support part 330 includes: a bearing 331 including an inner wheel part and an outer wheel part, each rotating independently, wherein the outer wheel part is installed to the rotation plate part 310; and a support body 332 being provided on one side thereof with a bearing stationary shaft 332a being installed to the inner wheel part of the bearing 331 and being provided on an opposite side thereof with a ball body 332b inserted into the ultrasonic wave generating unit 200.

The ultrasonic wave generating unit 200: is coupled with the ball body 332b to be allowed to freely rotate in X, Y, and Z axis directions with the ball body 332b as the center; is tilted based on the axial direction of the motor shaft 110 with one surface opposite to a side where the transducer 210 is installed being in contact with each end of the plurality of protruding parts 320; and emits ultrasonic waves through the transducer 210 in a tilted direction, as an example.

The rotation plate part 310: is provided internally with a bearing insertion part 310a in which the bearing 331 is inserted; and is formed with an axial hole 310b which is communicated with the bearing insertion part 310a and allows the bearing stationary shaft 332a to pass through.

The bearing 331 has the outer wheel part fastened and installed to the rotation plate part 310 within the bearing insertion part 310a, wherein the rotation plate part 310 may include a first rotation plate body 311 and a second rotation plate body 312 both of which include a portion of the bearing insertion part 310a, respectively, and are coupled with and separated from each other.

The first rotation plate body 311 is installed and fastened to the motor shaft 110, and a portion of the bearing insertion part 310a is formed in a middle of a lower side of the first rotation plate body 311. In addition, the second rotation plate body 312 is coupled with and separated from a bottom of the first rotation plate body 311, with a remaining portion of the bearing insertion part 310a being formed on an upper surface, and an axial hole 310b being formed in a middle to allow the bearing insertion part 310a to pass through it.

The first rotation plate body 311 and the second rotation plate body 312 are coupled with and separated from a commonly known coupling structure such as a bolt, a screw, and so on, as an example. Furthermore, various modifications may be implemented with a commonly known coupling structure allowed to be decoupled, as is clearly stated here.

That is, the rotation plate part 310 rotates independently from the support body 332 when the motor shaft 110 of the rotating motor 100 rotates, and the support body 332 does not rotate even when the motor shaft 110 rotates.

The support body 332 may include: a first supporter 333 being provided with the bearing stationary shaft 332a; and a second supporter 334 having a ball support fixture 332c provided with the ball body 332b to an end thereof and protruded therefrom, and being coupled with and separated from the first supporter 333.

A magnet is embedded in one of the first supporter 333 and the second supporter 334, and a magnetic substance capable of being attached to the magnet by a magnetic force is provided in a remaining one of the first supporter 333 and the second supporter 334, whereby the first supporter 333 and the second supporter 334 are coupled with and separated from each other by the magnetic force of the magnet, as an example.

The first magnet 333a and the second magnet 334ab each capable of being attached to each other with magnetic force thereof are inserted into the first supporter 333 and the second supporter 334, respectively, wherein the first magnet 333a and the second magnet 334a are disposed to face each other in different poles.

It is preferable that the first supporter 333 and the second supporter 334 are strongly attached with a magnetic force of the first magnet 333a and the second magnet 334a, whereby the first supporter 333 and the second supporter 334 are maintained in a stable state being coupled with each other without being decoupled from each other during an operation of the therapeutic ultrasonic wave generating device according to the present invention.

The first supporter 333 and the second supporter 334 are to allow a different ultrasonic wave generating unit 200 to be used by replacing the ultrasonic wave generating unit 200 by decoupling the first supporter 333 and the second supporter 334 from each other.

That is, the ultrasonic wave generating unit according to the present invention enhances therapeutic performance by moving the focus of ultrasonic waves on the same plane at a uniform depth under the skin and thus enables the energy to be applied uniformly and evenly within the part to be treated. When a depth of the focus of the ultrasonic wave has to be changed depending on a patient or a location of the part to be treated, an ultrasonic wave generating unit 200 having a different focus location of ultrasonic waves may be easily replaced.

The motor shaft 110, the bearing stationary shaft 332a, and the ball body 332b are disposed on a coaxial line, thereby having a common center of rotation, as an example.

Meanwhile, the therapeutic ultrasonic wave generating device according to the present invention may further include a division part 600 dividing an ultrasonic wave generating space 500b being disposed with the ultrasonic wave generating unit 200 therein and being filled with a medium for transmission of the ultrasonic wave therein in an inner space of the cartridge casing unit 500.

The division part 600 is a division film body 610 allowed to be freely folded and spread, wherein an inner side of the division part 600 is fastened to surround a periphery of the ultrasonic wave generating unit 200, and an outer side thereof is fastened to surround an inner peripheral surface of the cartridge casing unit 500, as an example.

The division film body 610 seals an ultrasonic wave generating space 500b in which a lower part of the ultrasonic wave generating unit 200, i.e., a section in which the transducer 210 generating ultrasonic waves is provided, is disposed, wherein an inner hollow section of the division film body 610 is fastened surrounding an upper section periphery of the ultrasonic wave generating unit 200, and the outer periphery thereof blocks a gap between the ultrasonic wave generating unit 200 and the cartridge casing unit 500 by being fastened to an inner peripheral surface of the cartridge casing unit 500.

The division film body 610 has an excellent strain rate, thereby being allowed to freely folded and spread, and is formed of materials such as resin, synthetic rubber, water-repellent cloth, and so on, that can block the ultrasonic wave generating space 500b, as an example. Furthermore, the division film body 610 is allowed to be made of any materials which are waterproof and allowed to be freely folded and spread, as is clearly stated here.

The division film body 610 does not interfere with an operation of the ultrasonic wave generating unit 200 by being freely folded and spread when the ultrasonic wave generating unit 200 is continuously tilted at an equal degree angle with a constant radius of 360 degrees by a rotation of the rotation plate part 310. Accordingly, the ultrasonic wave generating unit 200 is allowed to be operated smoothly.

A medium such as water having low ultrasonic wave loss factor is filled in the ultrasonic wave generating space 500b to prevent a loss of ultrasonic waves emitted from the transducer 210 generating ultrasonic waves for a medical treatment. Besides water, any fluid having a lower ultrasonic wave loss factor than water may be filled inside the ultrasonic wave generating unit 200, as is clearly stated here.

The cartridge casing unit 500 includes: a base plate installation part 510 being installed to and separated from a lower part of the header housing unit 400, having a first PCB 710 and a second PCB 720 being installed thereto and separated therefrom to control operation of the transducer 210, and being provided with the hollow section allowing the ultrasonic wave generating unit 200 to pass through it; an external casing part 520 being installed to and separated from the base plate installation part 510, and being provided on a bottom part with a first ultrasonic wave penetration window 521 allowing the ultrasonic wave to pass through; and an internal casing part 530 being inserted in the external casing part 520, and allowing the ultrasonic wave to pass through by being communicated with the first ultrasonic wave penetration window 521 on a bottom part, wherein an ultrasonic wave penetration unit 500a of a transparent or translucent material blocking the first ultrasonic wave penetration window 521 and a second ultrasonic wave penetration window 531 is inserted and fastened in-between the external casing part 520 and the internal casing part 530, as an example.

The ultrasonic wave penetration unit 500a is a transparent or translucent film and has a portion of an outer periphery thereof being inserted in-between the external casing part 520 and the internal casing part 530 between the first ultrasonic wave penetration window 521 and the second ultrasonic wave penetration window 531, thereby sealing the ultrasonic wave generating space 500b by blocking the first ultrasonic wave penetration window 521 and the second ultrasonic wave penetration window 531.

Figure 3:
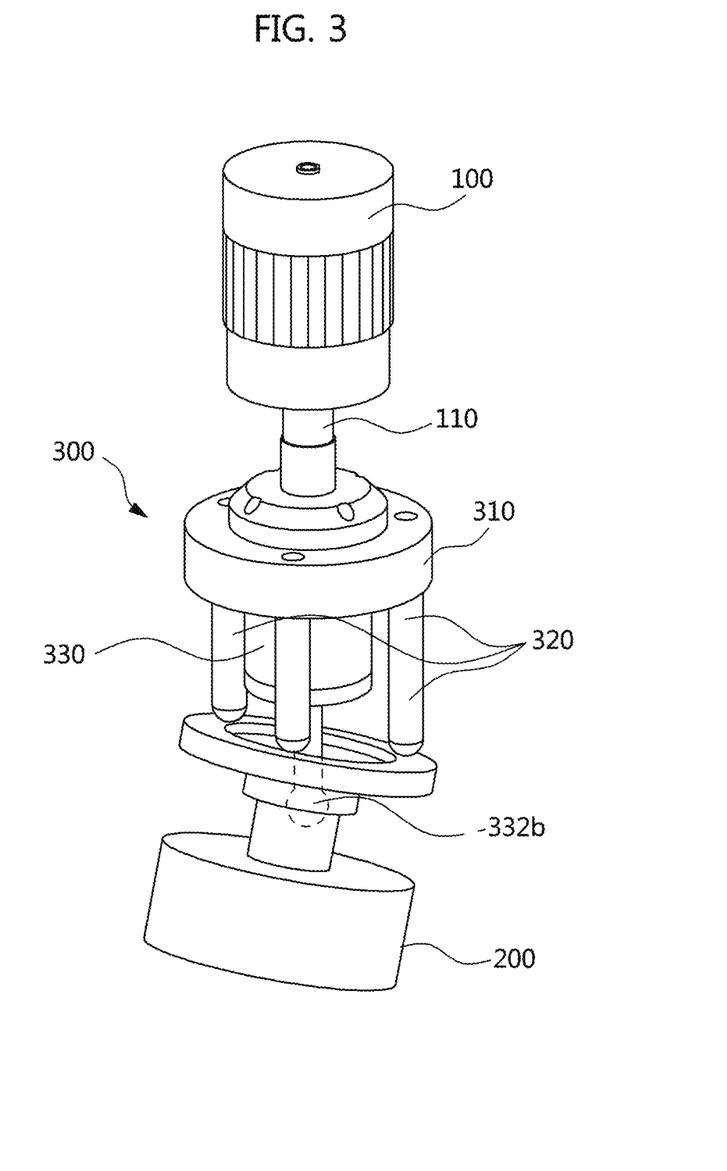
FIGS. 3 and 4 are exploded perspective views illustrating examples of operation of a therapeutic ultrasonic wave generating device according to the present invention.
Figure 4:
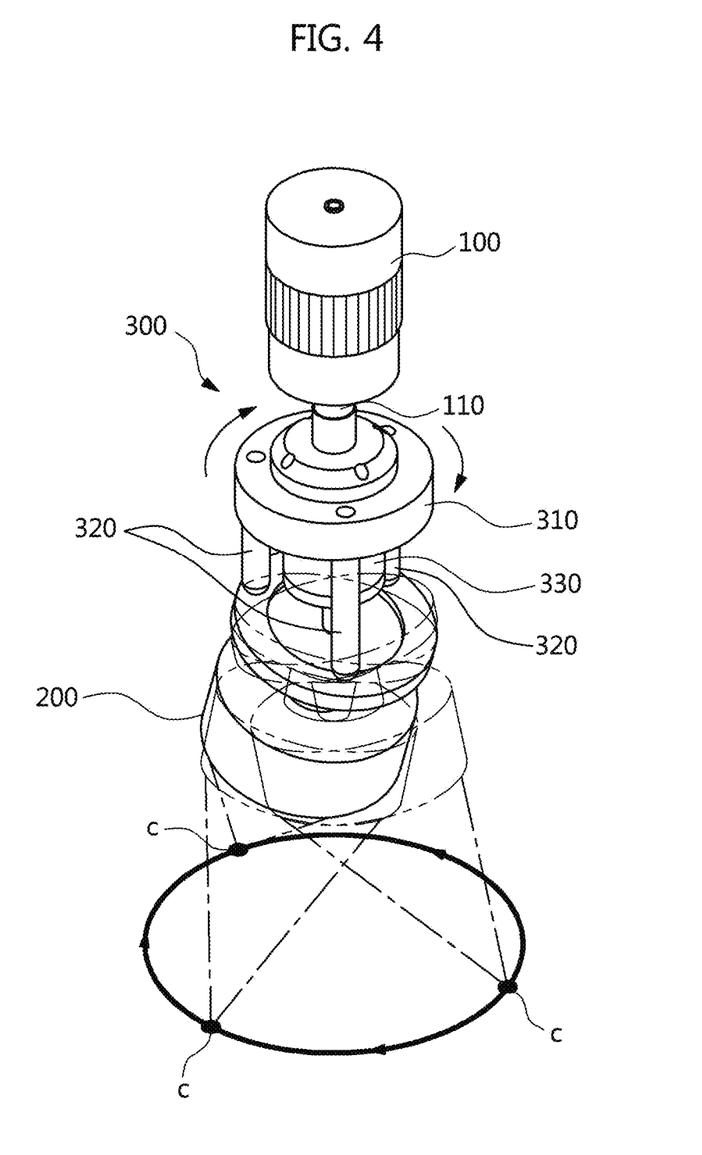

FIG. 3 is a schematic diagram illustrating an example where the therapeutic ultrasonic wave generating device according to the present invention is operating, and FIG. 4 is a schematic diagram illustrating an example where the focus C of the ultrasonic waves are moved in a circle on the same plane in the therapeutic ultrasonic wave generating device according to the present invention.

With reference to FIGS. 3 and 4, the therapeutic ultrasonic wave generating device according to the present invention is disposed to force the ultrasonic wave generating unit 200 to be tilted based on the axial direction of the motor shaft 110 by the plurality of protruding parts 320 protruding with different heights from each other on the rotation plate part 310, and forms the focus C by emitting the ultrasonic waves in a tilted direction.

Accordingly, the transducer 210 installed in the ultrasonic wave generating unit 200 is also tilted, wherein a slope of the ultrasonic wave generating unit 200 may be appropriately adjusted depending on a size of the cartridge casing unit 500 and a size of the transducer 210.

In addition, the therapeutic ultrasonic wave generating device according to the present invention has the rotation plate part 310 rotated by an operation of the rotating motor 100 in a state that the ultrasonic wave generating unit 200 is disposed to be tilted based on the axial direction of the motor shaft 110. Accordingly, moving to draw a circle with a radius of 360 degrees by a rotation of the rotation plate part 310 in a state maintained with the plurality of protruding parts 320 having heights different from each other being in contact with a top surface of the ultrasonic wave generating unit 200, the plurality of protruding parts 320 having heights different from each other forces the ultrasonic wave generating unit 200 to be continuously tilted to have an equal degree angle with the ball body 332b as a center.

Accordingly, the focus C of the ultrasonic wave emitted from the ultrasonic wave generating unit 200 is forced to move in the circle on the same plane.

That is, the present invention may enable the focus C of the ultrasonic wave to be moved on the same plane at a uniform depth under the skin and thus the energy to be applied uniformly and evenly within the part to be treated, thereby enhancing therapeutic performance.

The present invention has an advantage of further enhancing therapeutic performance by forming the focus C of the ultrasonic wave in a circle having a constant radius at a uniform depth under the skin, thereby applying energy uniformly within the radius.

Those skilled in the art will appreciate that various modifications, additions and substitutions are possible within a fundamental scope and technical concept of the present invention. Accordingly, the technical protection scope of the present invention should be defined based on the technical concept of the attached claims.

The invention claimed is:

1. A therapeutic ultrasonic wave generating device, the device comprising:
   a rotating motor;
   an ultrasonic wave generating unit comprising a transducer, the ultrasonic wave generating unit configured to generate ultrasonic waves; and
   a focus rotation movement unit configured to move a focus of the ultrasonic waves generated by the ultrasonic wave generating unit in a circle on a same plane by receiving a transmission of rotational force of the rotating motor,
   wherein the focus rotation movement unit comprises:
   a rotation plate part configured to rotate with a rotating axis of the rotating motor as a center by receiving the transmission of the rotational force of the rotating motor; and
   a plurality of protruding parts configured to be disposed separately from each other on the rotation plate part, and to force the ultrasonic wave generating unit to be tilted with the rotating axis of the rotating motor as the center with each end thereof being in contact with the ultrasonic wave generating unit,
   wherein the focus rotation movement unit is configured such that, when the rotation plate part and the plurality of protruding parts rotate, an angle swept by the rotation plate part and the plurality of protruding parts is equal to an angle swept by the focus on the circle on the same plane.

2. The device of claim 1, wherein a center of the circle along which the focus is moved is located at the rotating axis of the rotating motor.

3. The device of claim 1, wherein the focus is moved in the circle at a uniform depth under a skin of a patient.

4. The device of claim 1, wherein the ultrasonic wave generating unit is configured to be tilted based on an axial direction of a motor shaft of the rotating motor, and emits the ultrasonic waves through the transducer in a tilted direction.

5. The device of claim 1, wherein the angle swept by the rotation plate part and the plurality of protruding parts is 360 degrees.

6. The device of claim 1, wherein each protruding part of the plurality of protruding parts has heights different from each other.

7. The device of claim 1, wherein each protruding part of the plurality of protruding parts is disposed at an equal distance from the rotating center of the rotation plate part.

8. The device of claim 1, wherein the focus rotation movement unit is configured such that the rotation plate part and the plurality of protruding parts can be repeatedly rotated.

9. The device of claim 1, further comprising a support part configured to support the ultrasonic wave generating unit to force the ultrasonic wave generating unit to be tilted toward the every direction of 360 degrees by the rotation of the rotation plate part.

10. The device of claim 9, wherein the support part comprises:
    a bearing comprising an inner wheel part and an outer wheel part, each rotating independently, wherein the outer wheel part is connected to the rotation plate part; and a support body being provided on one side thereof with a bearing stationary shaft being connected to the inner wheel part of the bearing and being provided on an opposite side thereof with a ball body inserted into the ultrasonic wave generating unit, wherein the ultrasonic wave generating unit is coupled with the ball body to be allowed to freely rotate in X, Y, and Z axis directions with the ball body defining a center of rotation of the ultrasonic wave generating unit.

11. The device of claim 10, wherein the support body further comprises:
   a first supporter comprising the bearing stationary shaft; and
   a second supporter having a protruded ball support fixture comprising the ball body attached to an end of the second supporter, and being coupled with and separated from the first supporter.

12. The device of claim 11 wherein a first magnet is embedded in the first supporter, wherein a second magnet is embedded in the second supporter, and wherein the first supporter and the second supporter are coupled with each other by a magnetic force provided by the first and second magnets.

13. The device of claim 1, further comprising:
   a header housing unit being connected with the rotating motor therein; and
   a cartridge casing unit being connected with the ultrasonic wave generating unit therein,
   wherein the cartridge casing unit comprises an ultrasonic wave penetration unit of a transparent or translucent material through which the ultrasonic waves pass in a direction that the ultrasonic waves are emitted from the ultrasonic wave generating unit.

14. The device of claim 13, further comprising:
   a division part configured to divide an ultrasonic wave generating space disposed with the ultrasonic wave generating unit therein, the ultrasonic wave generating space being filled with a medium for transmission of the ultrasonic waves in an inner space of the cartridge casing unit.

15. The device of claim 14, wherein the division part is a division film body configured to be freely folded and spread, wherein an inner side of the division part is fastened to surround a periphery of the ultrasonic wave generating unit, and an outer side of the division part is fastened to surround an inner peripheral surface of the cartridge casing unit.

* * * * *